United States Patent

Cabados et al.

[11] Patent Number: 6,007,501
[45] Date of Patent: Dec. 28, 1999

[54] THERAPEUTIC MASSAGING APPARATUS

[76] Inventors: Rick Henry Cabados; Susan Ann Burke, both of 2680 Forest Park Rd., Jamul, Calif. 91935

[21] Appl. No.: 08/786,147

[22] Filed: Jan. 21, 1997

[51] Int. Cl.[6] .......................... A61H 15/00; A61H 15/02
[52] U.S. Cl. ........................ 601/15; 601/71; 601/131; 601/132; 601/134; 601/143
[58] Field of Search .................... 601/15, 134–7, 601/132, 124, 110, 143, 71, 131, 129, 128, 118

[56] References Cited

U.S. PATENT DOCUMENTS

| | | |
|---|---|---|
| 876,491 | 1/1908 | Rohwer . |
| 898,379 | 9/1908 | Liebhardt . |
| 2,304,235 | 12/1942 | Boots . |
| 2,777,440 | 1/1957 | Baker . |
| 3,921,620 | 11/1975 | Nakayama ................................ 600/15 |
| 4,095,587 | 6/1978 | Ishikawa . |
| 4,480,596 | 11/1984 | Shumiyashu . |
| 4,716,898 | 1/1988 | Chauve et al. ...................... 601/134 X |
| 4,796,616 | 1/1989 | Panahpour . |
| 4,846,159 | 7/1989 | Anzai et al. ............................ 601/128 |
| 4,944,289 | 7/1990 | Matthews ................................ 601/134 |
| 4,974,582 | 12/1990 | Johnson .................................. 601/134 |
| 5,036,865 | 8/1991 | Keaton . |
| 5,289,960 | 3/1994 | Kelly et al. . |
| 5,545,456 | 8/1996 | Suida .................................. 601/137 X |
| 5,628,772 | 5/1997 | Russell ................................ 601/131 X |

*Primary Examiner*—Danton D. DeMille
*Attorney, Agent, or Firm*—Presseisen & Reidelbach, PLC; Charles F. Reidelbach, Jr.

[57] ABSTRACT

A therapeutic massaging apparatus having a pair of resilient balls adjustably positioned in a flexible container, wherein a strap assembly is connected to opposing ends of the container so as to maintain the container in a pre-selected position upon the user. The present invention also integrates other therapeutic principals by utilizing a pocket formed in the container for allowing the user to enjoy the benefits of traditional acupressure therapy while simultaneously enjoying the well known therapeutic effects of magnetism, gemstones, crystals and/or herbs.

14 Claims, 2 Drawing Sheets

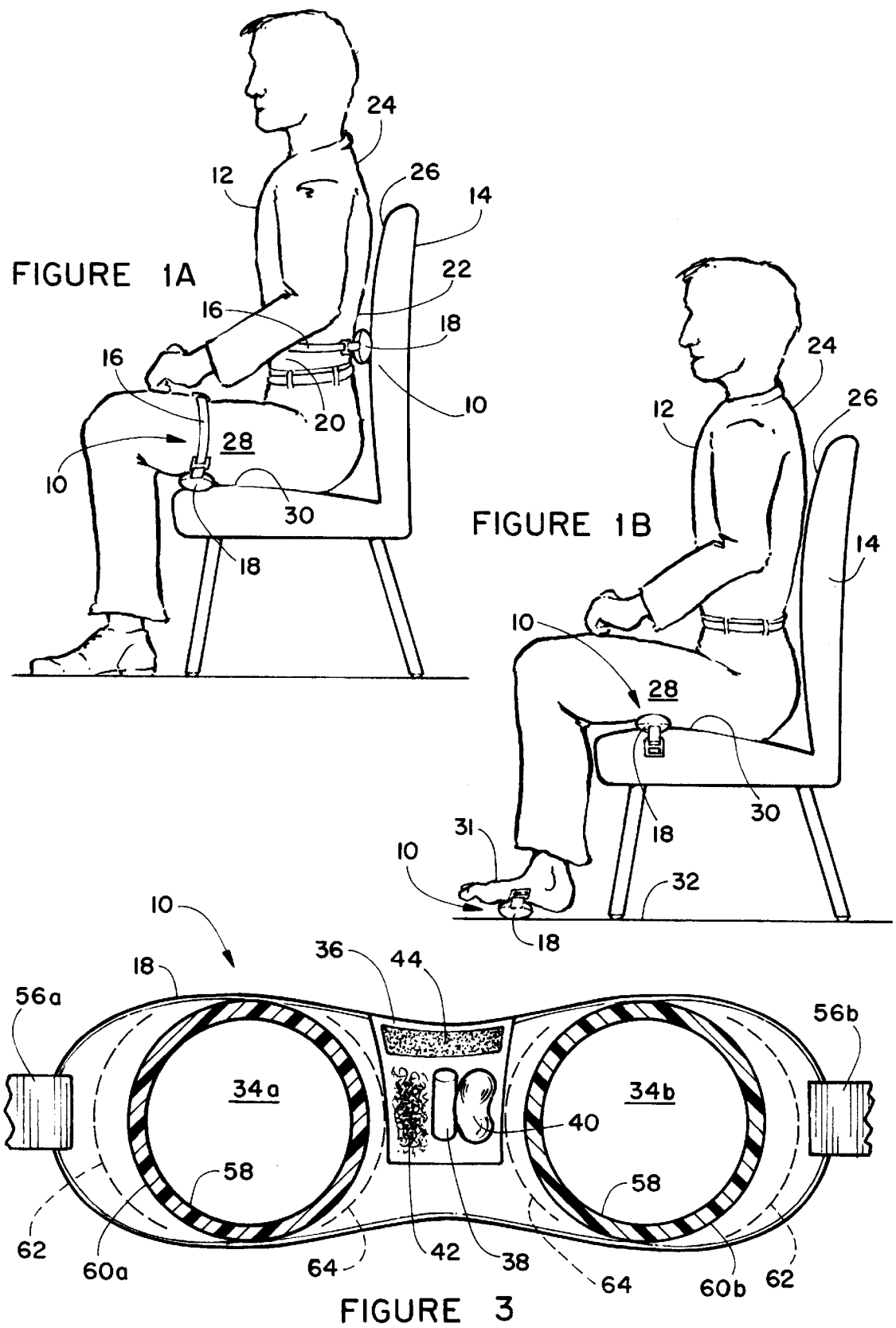

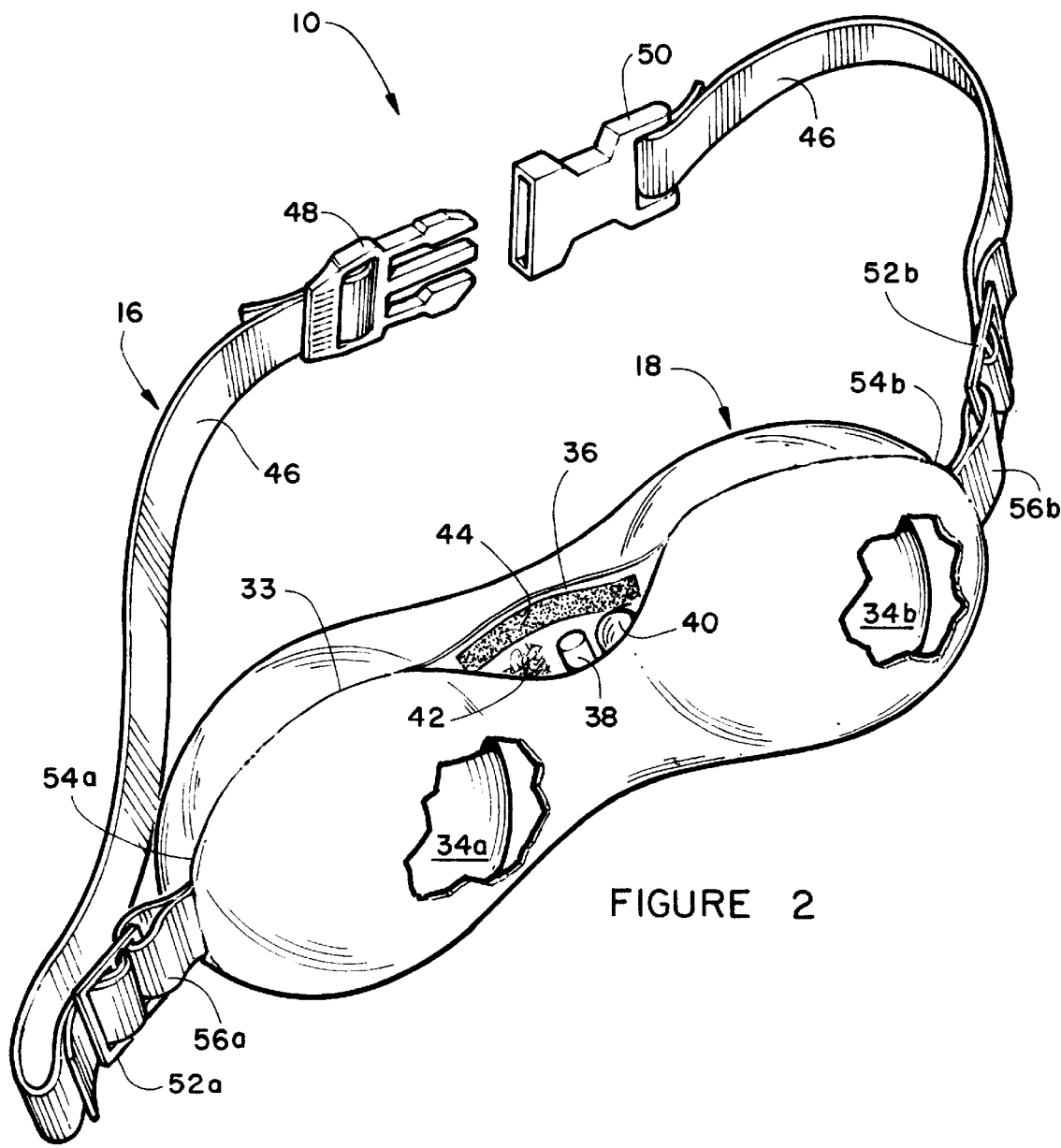

THERAPEUTIC MASSAGING APPARATUS

BACKGROUND OF THE INVENTION

1. Field of the Invention

The present invention relates generally to a massaging apparatus for relieving ailments and pain emanating from various areas on the human body of a user. More specifically, the present invention provides a therapeutic massaging apparatus having a pair of resilient balls selectively positioned in a flexible container which can be worn on the body of the user. Moreover, the present invention is adaptable for containing one or more of the following therapeutic objects; magnet, gemstone, and herb.

2. Description of the Related Art

A 5,000 year old Chinese tradition, known as acupressure therapy, teaches the placement of pressure on set points of the body to treat tension-related ailments, muscular discomfort, and illness prevention. The pressure is thought to release blocked energy along the body's energy channels. Over the years, many lines of massaging devices have been developed which implement this concept. One line of massaging devices which have been known to provide a satisfying massaging effect are those which apply the pressure of resilient balls upon various parts of a human body. Examples of prior art devices of that type are shown in U.S. Pat. No. 2,777,440 granted to Baker in 1957 and U.S. Pat. No. 4,796,616 granted to Panahpour in 1989.

Prior art massaging devices similar to the type shown above have had the unfortunate drawback of not being adaptable to be worn on the body of the user. This disadvantage has presented a significant limitation in the effective application of these devices when the user is frequently moving, particularly when the user is either in a restful or unaware state of mind, such as sleeping, or when the assistance of another person is necessary to administer the massage but is either unavailable or undesired. Accordingly, there is a need for a massaging device which would allow the user to enjoy the beneficial effects of an acupressure therapy massage despite physical movement in his or her position or circumstance, including while the user is sleeping.

It is also well known that the application of a magnetic flux to a human body is effective for promoting health and well being, reducing stiffness or pain in various muscles, and for improving blood circulation, although the theoretical analysis of those effects are still in question. One common theory is that magnetism critically influences iron, a key element which can be traced to substantially all parts of the human body and which critically effects blood circulation. Examples of prior art devices of that type are shown in U.S. Pat. No. 4,095,587 granted to Ishikawa in 1978 and U.S. Pat. No. 4,162,672 granted to Yazaki in 1979. Furthermore, it is well known that the application of either or the combination of gemstone, crystal and herb to a human body is effective for promoting the emotional well being. Diane Stein, *Healing with Gemstones and Crystals* (1996); Patricia Kaminski & Richard Katz, *Flower Essence Repeutory* (1994).

Until now, however, there have been no known devices which integrate the above mentioned therapeutic principals into a singular massaging apparatus. Accordingly, there is a need for an apparatus which would allow a user to enjoy the benefits of a physical massage implementing acupressure concepts while simultaneously enjoying the well known therapeutic effects of magnetism, gemstone, crystal and/or herb. Although seemingly simple in design and low in cost no prior device can accomplish the clearly effective results of the instant invention.

SUMMARY OF THE INVENTION

It is an object of the present invention to provide a therapeutic massaging apparatus which is adaptable to be worn on the body of the user so as to maintain the apparatus in a pre-selected position upon the user despite frequent movement of the user's body.

It is another object of the present invention to provide an integrated therapeutic massaging apparatus which allows a user to enjoy the well known benefits of a physical message through acupressure therapy while simultaneously enjoying any one or combination of therapeutic effects resulting from magnetism, gemstones, crystals and/or herbs.

It is yet another object of the present invention to provide a massaging apparatus which is inexpensive to manufacture and which will thus bring beneficial results to many people at little cost.

The present invention provides a therapeutic massaging apparatus which utilizes an enclosed flexible container for holding a pair of adjustable resilient balls. The container is designed to be worn on the body of the user by means of a removable strap assembly which maintains the apparatus in a pre-selected position upon the user despite physical movement of the user's body.

The present invention also integrates traditional eastern therapeutic principals by utilizing a pocket formed in the container for allowing the user to enjoy the benefits of acupressure therapy while simultaneously enjoying the well known therapeutic effects of magnetism, gemstones, crystals and/or herbs.

The novel features of this invention, as well as the invention itself, both as to its structure and its operation will be best understood from the accompanying drawings, taken in conjunction with the accompanying description, in which similar reference characters refer to similar parts, and in which:

BRIEF DESCRIPTION OF THE DRAWINGS

FIG. 1A is an overall perspective view of the present invention as applied to both the lower back and thigh muscles of a user while seated in a chair;

FIG. 1B is an overall perspective view of the present invention with the strap assembly removed and as applied to the thigh muscles and foot of a user while seated in a chair;

FIG. 2 is a perspective view of the preferred embodiment of the present invention with portions of the container cut away;

FIG. 3 is a longitudinal cross-sectional view of the present invention taken along the seam of the container.

DESCRIPTION OF THE PREFERRED EMBODIMENT

FIGS. 1A and 1B illustrate the therapeutic massaging apparatus 10 according to the present invention as applied to the human body of a user 12 seated in a chair 14. Referring initially to FIG. 1A, the apparatus 10 includes a strap assembly 16 which is adjustable in length to pass around the body of the user 12 and securely position the container 18 against the painful ailment or stiff muscle area of the user 12. In one application, the present invention is shown with the strap assembly 16 placed around the torso 20 of the user 12 so as to provide secure positioning of the container 18 upon selected back muscles 22 of the user 12. During use of the present invention with this application, the user 12 presses his or her back 24 toward the back 26 of the chair 14 so as to apply pressure against the container 18 of the present invention. The user 12 may move his or her back 24 up and down, sideways, and diagonally relative to the apparatus 10 to obtain the desired massaging effect. The apparatus 16 can be selectively repositioned along various areas of the back as is well known in the art of acupressure therapy.

In another application, the present invention is illustrated in FIG. 1A with strap assembly 16 placed around the thigh 28 of the user 12 so as to provide secure positioning of the container 18 upon a pre-selected area of the leg muscles of the user 12. As desired and as illustrated in FIG. 1B, the strap assembly 16 may be removed since the container 18 remains substantially in position as a result of the pressure exerted by the thigh 28 against the container 18 and chair seat 30. During use of the present invention in this application, the user 12 assumes a seated position in the chair 14 thereby receiving a massaging effect as a result of the pressure exerted by the thigh 28 against the container 18 and chair seat 30. In a similar manner, the user 12 may move his or her thigh 28 sideways and diagonally relative to the chair seat 30 to obtain the desired massaging effect.

Referring now to the illustration in FIG. 1B, the user 12 remains is a seated position, however, the strap assembly 16 has been removed to illustrate that the present invention is functional and has useful application despite the removal of the strap assembly 16. Additionally, another application of the present invention is presented and illustrated. More specifically, the apparatus 10 is placed between the foot 31 of the user 12 and the floor 32. Consequently, as pressure is applied to the container 18 by the foot 31 user 12, a massaging effect results. Again, the user 12 may move the foot 31 in various directions relative to the floor 32 to obtain the desired massaging effect as is well known in acupressure therapy.

It can be appreciated that the device of the present invention is particularly adapted for use by an individual without the assistance from another person. It is also to be understood that the above illustrations are only several ways in which the present invention can be utilized by the user 12. For example, the apparatus 10 may be strapped or positioned on the back 26 of a chair 14 (not shown) or other secure device.

Referring now to FIG. 2, the container 18 of the present invention is formed from a flexible material, preferably an elastic fabric such as nylon, spandex, cotton, or any combination thereof. The container 18 may be created by any means well known in the art, preferably by folding a rectangular shaped sheet of fabric made of a cotton/spandex blend and sewing the edges together to form a seam 33 as shown in FIG. 2. The container 18 is designed to receive multiple resilient bodies 34a, b, each having substantially the same diameters while providing enough space to permit the lateral adjustment of the bodies 34a, b relative to one another. In the preferred embodiment pictured in FIG. 2, the resilient bodies 34a, b are a pair of commonly available racquetballs. To provide an enclosed flexible container consistent therewith, the size of the sheet of fabric is preferably 6 inches in width and 9 inches in length. However, it is to be appreciated that the present invention contemplates containers 18 of differing sizes and shapes depending upon the particular circumstances such as the size and shape of the enclosed resilient bodies 34a, b.

In accordance with the present invention, one or more compartments 36 are formed in the container 18, each compartment 36 containing at least one object selected from the group consisting of a magnet 38, a gemstone and/or crystal 40, and an herb 42. For purposes of simplicity rather than limitation, only one compartment 36 is illustrated in the preferred embodiment shown in FIG. 2. The compartment 36 is a pocket formed in center of the container 18 intermediate balls 34a, b, and preferably has a securing means 44 for opening and closing the pocket to allow the user 12 to access the objects from the compartment 36. The securing means 44 can be formed using any well known means in the art such as velcro, button, snaps or a zipper.

According to the preferred embodiment, the strap assembly 16 includes a strap 46 which is attached to a male buckle 48, female buckle 50, and two adjustor buckles 52a, b. As shown, the strap 46 is connected to opposing ends 54a, b of the container 18. Preferably, this is accomplished by passing a portion of the strap 46 through each adjustor buckle 52a, b, and sewing each respective portion of the strap 46 directly to the respective ends 54a, b of the container 18 to form loops 56a, b. However, the strap 46 may be made removable by any means well known in the art.

The strap 46 is preferably made of an elastic material such as nylon, but can be made from a variety of material types. The strap portion 46 attached to adjustor buckle 52b has one end freely looped and threaded through adjustor buckle 52b, and the other end looped through the female buckle 50, folded and stitched to secure. The strap portion 46 attachable to adjustor buckle 52a has one end freely looped and threaded through adjustor buckle 52a, and the other end of looped through the male buckle 48, folded and sewn to secure. Preferably each strap portion 46 has a length which can be adjusted to accommodate different waist and thigh sizes, making the total strap assembly 16 adjustable from a minimum of 10 inches to a maximum length of 40 inches. The strap assembly 16 is constructed so the user 12 can easily fasten the buckle 48, 50 at the center of the waist or thigh. After the buckle 48, 50 is snapped in place, the strap 46 can be comfortably secured by adjusting the length of the strap 46 through respective adjustor buckles 52a, b.

Referring now to FIG. 3, the resilient bodies 34a, b of the present invention are a pair of spherically shaped balls 34a, b which have a hollow center 58 and are compressible to a flattened egg shape when compression forces are applied thereto. The balls 34a, b are preferably made of rubber or a similar elastic material. Although there are a variety of commonly available balls 34a, b of the type herein mentioned, racquetballs have been found to produce best therapeutic results and are used in the preferred embodiment. The reason for the use of racquetballs is that their particular resiliency permits the continued flow of cerebral spinal fluids through the human body when pressure is applied to the ball against the body part of the user 12. The benefits of the continued flow of cerebral fluids during massage is well known to those skilled in the art of acupressure therapy practices. It is to be appreciated, however, that a wide variety of bodies 34a, b formed from a wide variety of materials could be used. Additionally, the bodies 34a, b may be of different shapes and sizes. For example, the bodies 34a, b could have protuberances (not shown) on their respective surfaces 60a, b to provide increased blood circulation during massage.

During use, the user 12 may adjust the balls 34a, b relative to one another within the container 18 so as assure desired lateral alignment of the balls 34a, b on the desired painful ailment or stiff muscle area. For example, referring back to FIG. 1, the user 12 may rest one ball 34a against the muscle on one side of the spine and the other ball 34b on the muscle on the other side other of the spine. The balls 34a, b may be adjusted from their most outermost position 62 to their most innermost position 64. Additionally, the user 12 may move his or her back 24 up and down, sideways, and diagonally relative to the apparatus 10 to effect the surrounding ailment or muscle area.

FIG. 3 shows the pocket 36 containing at least one object selected from the group consisting of a magnet 38, a gemstone and/or crystal 40, and an herb 42. It is well known that any one or combination of the group of objects above promote the emotional and physical well being of the human body. While gemstones/crystals 40 and herbs 42 have been known to assist in promoting emotional well being, exposing the human body to a magnetic field has been known to facilitate blood circulation and, hence, provide a favorable therapeutic effect on the removal of stiffness resulting from muscular pain and the like in the physical body.

In the preferred embodiment, the source of the magnetic field is provided by permanent ferrite magnet 38 having smooth oval shape and having dimensions of 0.1 inch by 0.21 inches. The strength of the magnetic field created by the magnet 38 may be in the range from 500 to 3600 gauss and is preferably about 2000 gauss at the surface of the magnet 38. The permanent magnet 38 is preferably designed with north and south poles uniquely aligned along the magnets edge for balanced multi-pole effect thus eliminating the necessity of selected positioning of the magnet 38 against the human body. However, if a single pole magnet is used, maximum results are established by positioning the north pole of the magnet towards the body. The multi-pole magnet 38 can be obtained from Oriental Medical Supply Company located in Braintree, Mass. It is to be appreciated that there are a variety of other magnets 38 commonly available which provide the therapeutic effectiveness of a magnetic field applied to the human body and which are equally effective for promoting good health.

In an alternative embodiment (not shown), the magnet 38 is fixedly or loosely positioned in the hollow area 58 of either or both resilient balls 34a, b. The placement of magnet 38 within balls 34a, b, can be accomplished during formation and manufacture of the balls 34a, b.

Although seemingly simple in design and inexpensive to construct, there is no prior art or device which anticipates or makes obvious the present massaging apparatus which is universal in application and which allows the user to enjoy the benefits of physical massage while simultaneously enjoying the therapeutic effects of magnetism, gemstones, crystals and/or herbs.

Since the invention is described and illustrated with reference to but a single preferred embodiment, and since numerous modifications and changes may become readily apparent to those skilled in the art after reading this disclosure, it should be understood that this invention should be limited only by the spirit and scope of the appended claims.

We claim:

1. A therapeutic massaging apparatus comprising:

a pair of resilient balls for providing a massage;

a container formed from a flexible material wherein said container is adapted to receive said pair of resilient balls located at opposite ends of the container and wherein said container permits adjustment of said balls relative to each other;

compartment formed in said container in a central region spaced between said resilient balls and containing at least one object selected from the group consisting of magnet, gemstone, crystal, and herb, each of said objects providing a therapeutic effect which is distinct and separate from said massage; and a removable strap assembly connected to opposing ends of said container and being adaptable to maintain said container in a pre-selected position upon the wearer.

2. An apparatus as recited in claim 1, further comprising a means for accessing said object from said container by the user.

3. A therapeutic massaging apparatus comprising:

a pair of resilient balls for providing a massage;

a container formed from a flexible material wherein said container is adapted to receive said pair of resilient balls located at opposite ends of the container and wherein said container permits adjustment of said balls relative to each other; and said resilient balls and containing a means positioned within said apparatus for exposing the user to a magnetic flux for therapeutic purposes.

4. An apparatus as recited in claim 2, wherein said means is a permanent magnet.

5. An apparatus as recited in claim 3, further comprising a strap assembly connected to opposing ends of said container and being adaptable to maintain said container in a pre-selected position upon the wearer.

6. A self-supporting therapeutic messaging apparatus comprising:

a plurality of resilient bodies for providing a massage;

a container formed from a flexible material wherein said container is adapted to receive said plurality of bodies located at opposite ends of the container and wherein said container permits adjustment of said plurality of bodies relative to one another;

a compartment formed in said container in a central region spaced between said resilient bodies and containing at least one object for therapeutic purposes; and a removable strap assembly connected to opposing ends of said container and being adaptable to maintain said container in a pre-selected position upon the wearer.

7. An apparatus as recited in claim 6, wherein said resilient bodies are a pair of balls.

8. An apparatus as recited in claim 7, where said balls are racquetballs.

9. An apparatus as recited in claim 7, wherein said balls have a hollow center and are compressible.

10. An apparatus as recited in claim 6, wherein said flexible material is also elastic.

11. An apparatus as recited in claim 6, wherein said strap assembly is adjustable in length to pass around the body of the wearer and securely position the container against the painful area of the wearer.

12. An apparatus as recited in claim 6, wherein said object a magnet.

13. An apparatus as recited in claim 9, further comprising a magnet, said magnet positioned within said hollow center of said balls.

14. An apparatus as recited in claim 6, further comprising a means positioned within said apparatus for exposing the user to a magnetic flux for therapeutic purposes.

\* \* \* \* \*